(12) United States Patent
Homer et al.

(10) Patent No.: US 8,024,133 B2
(45) Date of Patent: Sep. 20, 2011

(54) SYSTEM FOR DETECTING AND ESTIMATING CONCENTRATIONS OF GAS OR LIQUID ANALYTES

(75) Inventors: Margie L. Homer, Pasadena, CA (US); Darrell L. Jan, South Pasadena, CA (US); April D. Jewell, Medford, MA (US); Adam Kisor, Pasadena, CA (US); Kenneth S. Manatt, Tujunga, CA (US); Allison M. Manfreda, Pasadena, CA (US); Margaret A. Ryan, Pasadena, CA (US); Abhijit V. Shevade, Altadena, CA (US); Charles Taylor, Claremont, CA (US); Tuan A. Tran, Upland, CA (US); Shiao-Pin S. Yen, Altadena, CA (US); Hanying Zhou, Arcadia, CA (US)

(73) Assignee: California Institute of Technology, Pasadena, CA (US)

( * ) Notice: Subject to any disclaimer, the term of this patent is extended or adjusted under 35 U.S.C. 154(b) by 861 days.

(21) Appl. No.: 11/986,784

(22) Filed: Nov. 26, 2007

(65) Prior Publication Data

US 2010/0286929 A1 Nov. 11, 2010

Related U.S. Application Data

(60) Provisional application No. 60/861,617, filed on Nov. 29, 2006.

(51) Int. Cl.
*G06F 19/00* (2011.01)

(52) U.S. Cl. .......................................................... 702/24
(58) Field of Classification Search ...................... 702/24
See application file for complete search history.

(56) References Cited

U.S. PATENT DOCUMENTS

| | | | | |
|---|---|---|---|---|
| 3,953,173 | A * | 4/1976 | Obayashi et al. | 436/151 |
| 4,423,407 | A * | 12/1983 | Zuckerman | 338/34 |
| 4,502,321 | A * | 3/1985 | Zuckerman | 73/25.03 |
| 5,497,651 | A * | 3/1996 | Matter et al. | 73/23.2 |
| 6,455,319 | B1 * | 9/2002 | Lewis et al. | 436/151 |
| 2002/0017126 | A1 * | 2/2002 | DiMeo et al. | 73/31.05 |
| 2002/0192117 | A1 * | 12/2002 | Lewis et al. | 422/82.05 |
| 2003/0153088 | A1 * | 8/2003 | DiMeo et al. | 436/113 |
| 2004/0040841 | A1 * | 3/2004 | Gonzalez-Martin et al. | 204/406 |
| 2009/0214762 | A1 * | 8/2009 | Lewis et al. | 427/58 |

OTHER PUBLICATIONS

Birlasekaran et al., "Use of FFT and ANN techniques in monitoring of transformer fault gases", 1998, IEEE, pp. 75-78.*

* cited by examiner

*Primary Examiner* — Cindy Hien-Dieu Khuu
(74) *Attorney, Agent, or Firm* — Berliner & Associates

(57) ABSTRACT

A sensor system for detecting and estimating concentrations of various gas or liquid analytes. In an embodiment, the resistances of a set of sensors are measured to provide a set of responses over time where the resistances are indicative of gas or liquid sorption, depending upon the sensors. A concentration vector for the analytes is estimated by satisfying a criterion of goodness using the set of responses. Other embodiments are described and claimed.

9 Claims, 6 Drawing Sheets

SYSTEM FOR DETECTING AND ESTIMATING CONCENTRATIONS OF GAS OR LIQUID ANALYTES

PRIORITY CLAIM

This application claims the benefit of U.S. Provisional Application No. 60/861,617, filed 29 Nov. 2006.

GOVERNMENT INTEREST

The invention described herein was made in the performance of work under a NASA contract, and is subject to the provisions of Public Law 96-517 (35 USC 202) in which the Contractor has elected to retain title.

FIELD

The present invention relates to gas or liquid sensors, and systems for estimating concentrations of gases and liquids of interest.

BACKGROUND

Gas detecting sensors have many applications. One such application is to detect the presence of a dangerous gas, or to detect a gas whose presence indicates a dangerous situation. For example, NASA (National Aeronautics and Space Association) has sponsored research in detecting low concentrations of sulfur dioxide ($SO_2$) in closed environments, such as for example aboard the international space station or the space shuttle. $SO_2$ could be a probable breakdown product from leaking lithium-thionyl chloride batteries. $SO_2$ is a colorless gas or liquid under pressure with a pungent odor. Inhalation or exposure could have adverse effects on human health.

In addition to detecting various gases, or liquids, of interest, it may also be of utility to provide estimates of the concentrations of various gases or liquids of interest. For example, various industrial processes may require that various gases or liquids be present within some range of concentration levels. In other applications, some dangerous gases may be tolerated if their concentrations fall below some threshold level.

DESCRIPTION OF EMBODIMENTS

In the description that follows, the scope of the term "some embodiments" is not to be so limited as to mean more than one embodiment, but rather, the scope may include one embodiment, more than one embodiment, or perhaps all embodiments.

Figure 1:
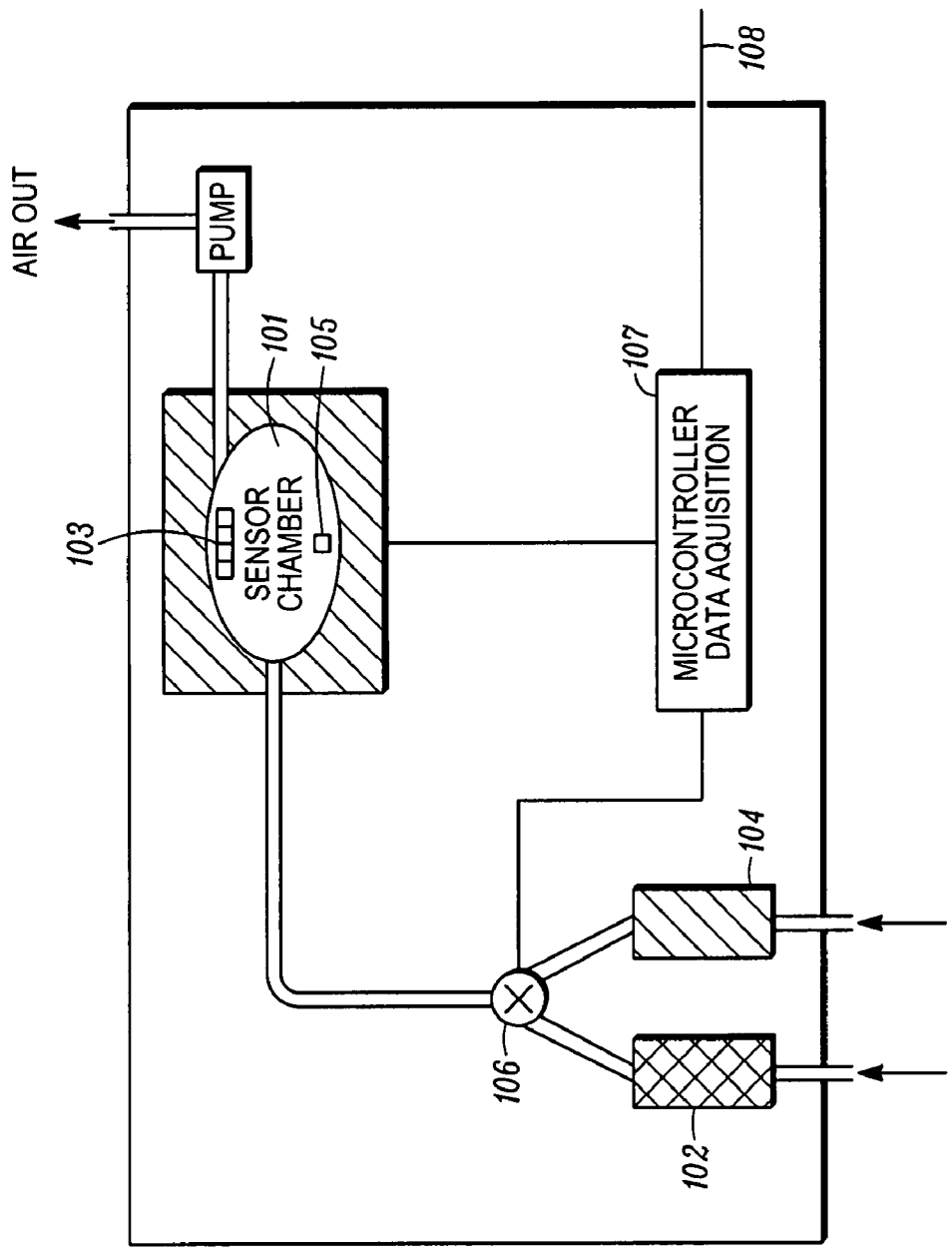
FIG. 1 illustrates a gas or liquid sensor system according to an embodiment.

FIG. 1 illustrates a sensor system according to an embodiment. Sensor chamber 101 includes a set of sensors for sensing various gases or liquids. This set of sensors, which may be termed a sensor array, is labeled as 103 in FIG. 1. The set of sensors may or may not be a contiguous set of sensors, although in the particular embodiment of FIG. 1 the set of sensors is illustrated as contiguous.

When the sensor system is operating, air is pumped from the surroundings into sensor chamber 101. The air is directed either through activated charcoal filter 102, which is put in line to provide clean air for baseline data, or though a dummy filter of glass beads, dummy filter 104, which is put in line to provide a pressure drop similar to that due to charcoal filter 102. Solenoid valve 106 is programmed to open the path to charcoal filter 102 and provide clean airflow for a pre-selected period of time at selected time intervals; otherwise, the air is directed through filter 104. When air enters sensing chamber 101, whether through dummy filter 104 or activated charcoal filer 102, the resistance of each sensor is measured. By processing the changes in resistances, embodiments provide for detection of various gases or liquids and estimation of their concentrations.

Sensor chamber 101 may also include other sensors. In the particular embodiment of FIG. 1, sensor chamber 101 includes humidity sensor 105 to measure humidity. As discussed later, measurements may be corrected for humidity. For some embodiments, humidity sensor 105 may be housed in a module separate from that containing sensor chamber 101.

Microcontroller and data acquisition module 107 controls the various components in the sensor system, measures resistance, and records the acquired measurements. Microcontroller and data acquisition module 107 may also include analog-to-digital conversion. Bus 108 provides an interconnect to other external components, such as a computer to process the resistance measurements.

Figure 2:
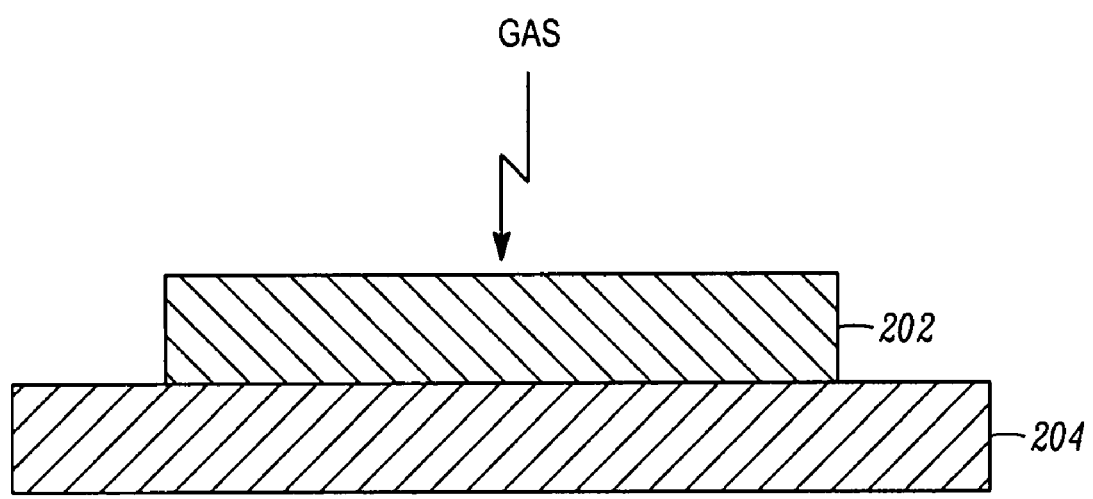
FIG. 2 illustrates a gas sensor according to an embodiment.

FIG. 2 illustrates a gas sensor according to an embodiment, where film 202 is formed on substrate 204. For some embodiments, film 202 may include a polymer or co-polymer. Film 202 adsorbs the gas, gases, liquid, or liquids of interest, which may be collectively referred to as the analyte. It is not known with certainty at this time if films according to the described embodiments absorb detectable analytes, adsorb detectable analytes, or some combination thereof. Accordingly, because the term sorption refers to the action of either absorption or adsorption, the term sorption and its variations will be used, indicating that a substance may be adsorbed, absorbed, or some combination thereof.

Some examples of analytes are ammonia, mercury, sulfur dioxide, acetone, dichloromethane, ethanol, Freon 218, methanol, 2-propanol, toluene, and formaldehyde. Of course, this is merely a list of examples, and embodiments are not limited to detecting these analytes, and some embodiments may be designed without necessarily being able to detect these listed analytes.

Substrate 204 may be flexible or rigid, and may be conductive or non-conductive, depending upon the way in which the sorbed gas is detected. Sorption of the analyte of interest causes a change in one or more physical properties of film 202. By measuring this change, detection of a sorbed gas may be accomplished, provided the change is sufficiently large to allow a measurement.

For example, for some embodiments, substrate 204 may be formed from silicon dioxide, and film 202 may include carbon so that the electrical resistance of the carbon changes, depending upon the sorption of the analyte by film 202. In this way, a resistance measuring device, in combination with the system of FIG. 1, may provide for the detection of a sorbed analyte. Other embodiments may be based upon changes in other physical properties of film 202. For example, sorption of a gas increases the mass of the resulting system, so that a measuring device sensitive to mass change may be used in the detection of the sorbed gas. As another example, the sorption of gas by a co-polymer in film 202 may cause swelling, causing dispersion in an acoustic wave traveling through the system comprised of substrate 204 and film 202. Accordingly, an acoustic measuring system may be part of a gas sensor system.

Figure 3:
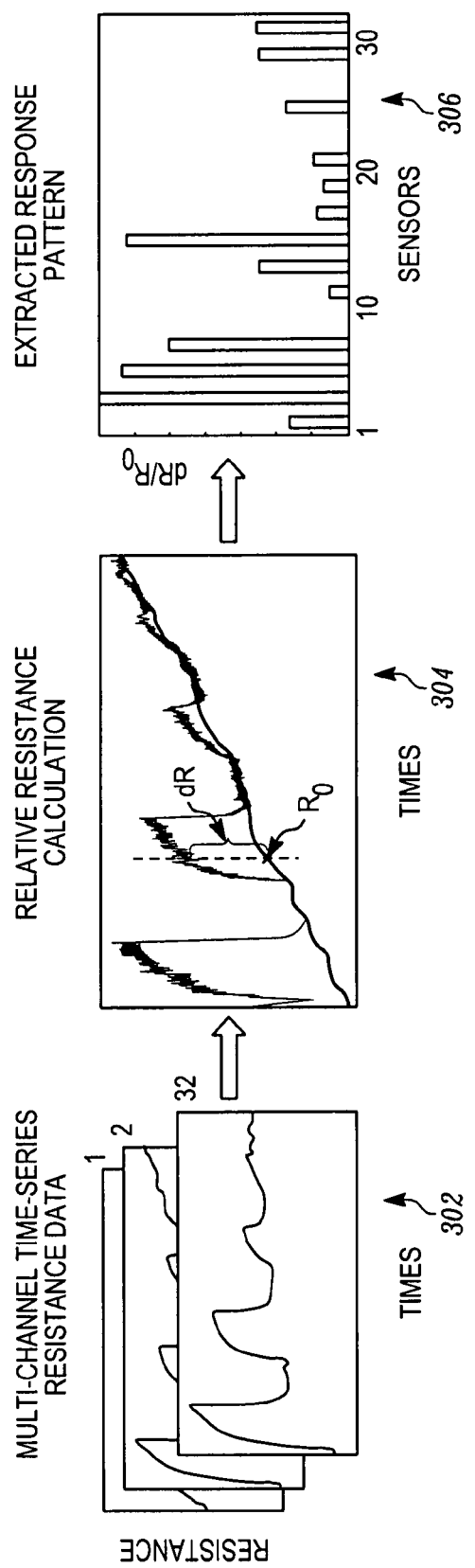
FIG. 3 illustrates resistance values and response patterns for a gas or liquid sensor according to an embodiment.

FIG. 3 illustrates the flow of signal processing applied to resistance measurements according to an embodiment of the present invention. For ease of discussion, the embodiment of FIG. 3 includes 32 sensors. The plots indicated by FIG. 3 need not actually be generated, but serve as representations of some of the signal processing functions performed by some embodiments. As indicated in plots 302, for each sensor a resistance is measured for some length of time.

Plot 304 is a resistance vs. time plot for a particular sensor, say sensor number 32. Shown in plot 304 is a baseline resistance, denoted as $R_0$. The baseline resistance is not necessarily measured directly, but may be estimated from resistance measurements. The resistance measurements may for some embodiments be obtained from raw resistance measurements after filtering has been applied. In the particular example of FIG. 3, an analyte has been introduced, and then removed, at various times, resulting in sudden changes in the measured resistance, R, as seen in plot 304. A time derivative of resistance, denoted as $$\frac{dR}{dt},$$

is estimated from the resistance measurements, where t denoted the time index. (In practice, computations may be performed in finite arithmetic, so that mathematical operations for some embodiments may be understood to be approximate with finite precision.) An event occurs when the time derivative $$\frac{dR}{dt}$$

is determined to be greater than some selected threshold, T. That is, an event is declared when $$dR/dt > T.$$

For some embodiments, a baseline resistance associated with an event may be the measured resistance value at the beginning of the event. Accordingly, associated with each event is a baseline resistance. Baseline resistance may be denoted as $R_0$. For some embodiments, the baseline resistance associated with an event may be taken at a time value other than the beginning of an event, or may be based upon filtered resistance measurements over some time interval associated with the event.

When an event is declared, a differential resistance dR associated with an event is provided by taking a difference in resistances. For some embodiments, the differential resistance may be the difference between the resistance associated with an event taken at some time, say the beginning of the event, and the baseline resistance associated with that event.

For the particular example of FIG. 3, the baseline resistance is seen to be increasing over time, and the differential resistance dR is seen to be decreasing. Baseline drift may be due to various causes, such as changes in temperature, humidity, flow pressure, etc. For some embodiments, the baseline drift may not look like that of plot 304.

The ratio of interest in plot 306 is $dR/R_0$. The ratio $dR/R_0$ may be referred to as a dynamic relative resistance change, where the term dynamic indicates that the baseline, as well as the differential in the resistance, may change with time. Plot 306 illustrates the dynamic relative resistance change for the 32 sensors, plotted as a bar graph. The ratio $dR/R_0$ may also be referred to as a response.

In general, the set of responses $dR/R_0$ for all the sensors will yield a pattern indicative, to some degree, upon the various analytes present. This pattern may be referred to as a fingerprint. Based upon a fingerprint, embodiments estimate the presence and concentration of various analytes. For some embodiments, the responses $dR/R_0$ are adjusted for humidity by subtracting out the expected humidity response. For example, let $dR(i)/R_0(i)$ denote the response for sensor i, where i is an index ranging over sensor labels. Let $dR_H(i)/R_{0H}(i)$ denotes the expected, or estimated, response of sensor i due to humidity alone. Then, some embodiments may form a humidity-corrected response by subtracting out $dR_H(i)/R_{0H}(i)$ from $dR(i)/R_0(i)$ for each sensor i.

The expected, or estimated, humidity response may be provided as follows for some embodiments. The set of responses may be measured in a controlled setting at various known humidity levels in which no detectable analytes are present so that a table of humidity responses for the various humidity levels may be generated and stored. In the field, the humidity level may be measured during real-time, such as for example with sensor 105 when air is being filtered by filter 102 and the path through dummy filter 104 is closed. A look-up procedure applied to the stored table may yield an estimate of the expected set of humidity responses.

As is well known, various interpolation and extrapolation techniques may be applied during a table look-up procedure. For example, in general the measured humidity level will not correspond exactly to any of the humidity level entries in the stored table, so that interpolation and extrapolation may be used. Other embodiments may correct the set of responses $dR(i)/R_0(i)$ for environmental factors other than humidity. For example, temperature may be taken into account.

Figure 4:
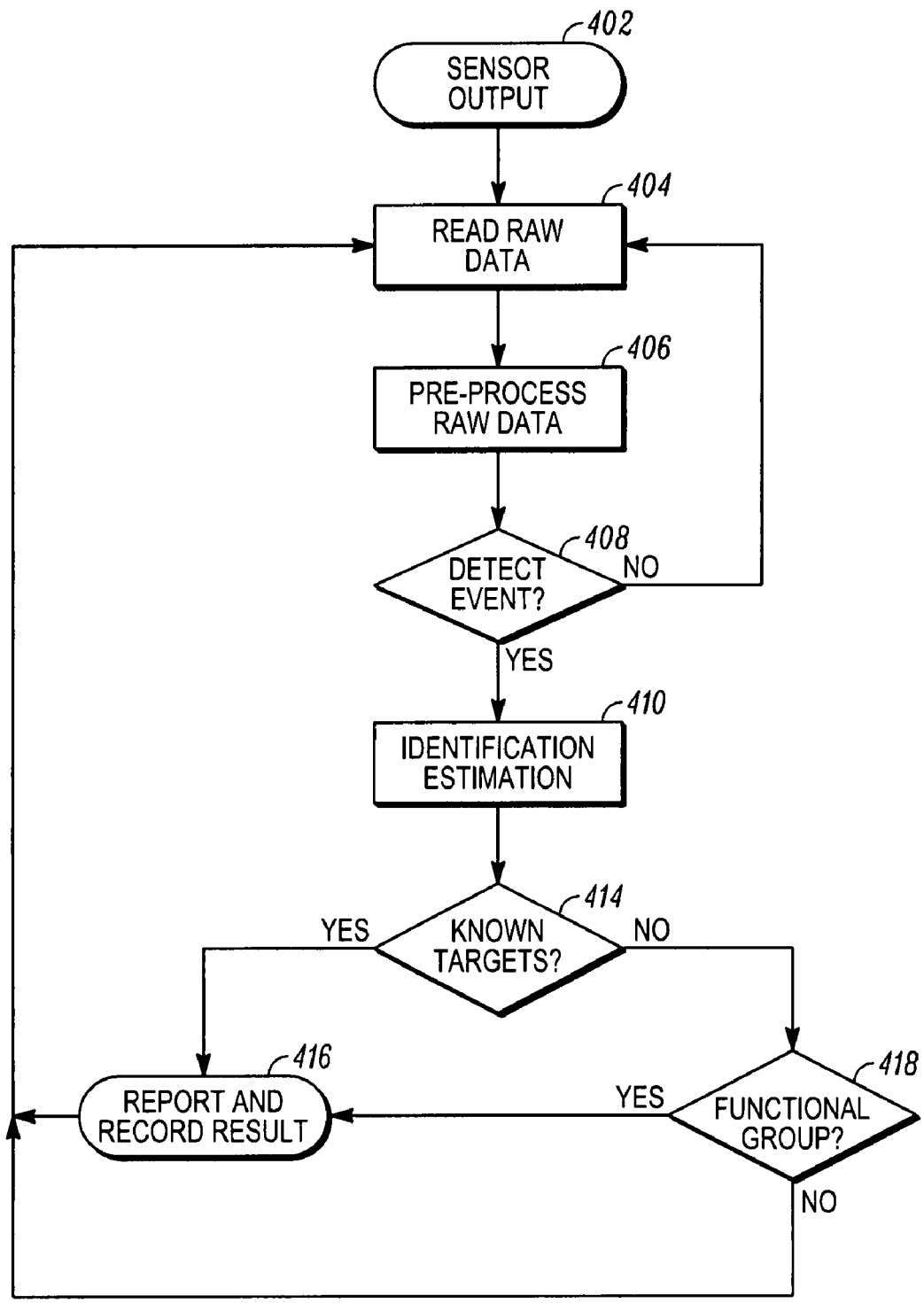
FIG. 4 illustrates a flow diagram for operation of a gas or liquid sensor system according to an embodiment.

FIG. 4 illustrates a flow diagram according to an embodiment. Some or all of the modules indicated in FIG. 4 may be realized by dedicated hardware, software, firmware, or some combination thereof. Raw data is read from the output of the sensors (modules 402 and 404). Module 406 may include various signal processing functions, such as for example filtering to estimate baseline data, and processing to detect events. If an event is not detected (module 408), control is brought to module 404 so that additional raw data may be read. If an event is detected, then identification of target analytes is performed (module 410).

If a known target analyte, or analytes, are detected (module 414), the estimated concentrations are reported out and recorded (module 416). In the particular embodiment of FIG. 4, if known target analytes are not detected, then various functional groups (families) may be identified (module 418). When testing for functional groups, subsets of the set of sensors are considered. That is, the fingerprint for a subset of the sensors is utilized in detecting whether a functional group is present. Different functional groups may correspond to different subsets of the sensors. Such functional groups may include, for example, an alcohol family (e.g., ethanol; 1-, 2-butanol; 1-, 2-propanol); an aromatic family (e.g., benzene; toluene; chlorobenzene; furan); a "one nitrogen" family (e.g., ammonia; acetonitrile; indole); and a ketone family (acetone; 2-butanone).

In the flow diagram of FIG. 4, note that control is brought to module 404 after module 408 if no event is detected, after module 418 if no functional group is detected, and after module 416 once a known target analyte or functional group is detected. However, such control flow is indicated merely for convenience, for in practice, various modules may be operating at the same time, or in a time-multiplexed fashion. Accordingly, the flow diagram indicated in FIG. 4 is not meant to imply any particular sequential order of operations. For example, module 404 may be operating in a continuous fashion, or in a near-continuous fashion if implemented in the digital domain, while other modules are operating.

In determining whether a target analyte is present based upon a fingerprint of responses, for example where the fingerprint of responses may be the set of dynamic relative resistance changes $$\frac{dR(i)}{R_0(i)}, i = 1, 2, \ldots, n,$$

where n is the number of sensors, some model of response versus the concentrations is chosen. This model may be represented abstractly as $$\vec{y} = f(A, \vec{x}),$$

where $\vec{y}$ is a vector of responses, $\vec{x}$ is a vector of concentrations, $f(\cdot,\cdot)$ is a function, and A is a system model parameter describing system characteristics. In practice, A is a set of parameters, but for simplicity it may be referred to as a parameter. The dimension of $\vec{y}$ is equal to or less than the number of sensors. For example, for some embodiments in which detection of a functional group is desired, the number of sensors under consideration may be a proper subset of the set of sensors, so that the dimension of $\vec{y}$ is less than the number of sensors. When detection of one or more target analytes is desired, for some embodiments the responses of all the sensors are processed, so that the dimension of $\vec{y}$ is equal to the number of sensors. For some embodiments the dimension of $\vec{x}$ is equal to the number of target analytes. In practice, the dimension of $\vec{x}$ is less than or equal to the dimension of $\vec{y}$.

It has been found that for some embodiments, interesting results were obtained with the following model $$\vec{y} = A_1 \vec{x} + A_2 \vec{x}^2, \quad (1)$$

where the superscript in $\vec{x}^2$ is a notational convenience to mean that the $i^{th}$ component of $\vec{x}^2$ is the square of the $i^{th}$ component of $\vec{x}$, and $A_1$ and $A_2$ are matrices modeling the system characteristics. If the convention is chosen such that the dimension of $\vec{y}$ is n and the dimension of $\vec{x}$ is m, then for some embodiments using the above model, $A_1$ and $A_2$ are n by m matrices.

The system modeling matrices $A_1$ and $A_2$ may be estimated by introducing known analytes of known concentrations, so that $\vec{x}$ and $\vec{x}^2$ are known and $\vec{y}$ is measured. Standard numerical techniques may then be applied to Eq. (1) to find an estimate of the system modeling matrices. For example, as is well known, minimum norm least squares methods using singular value decomposition may be applied to Eq. (1) to find estimates of $A_1$ and $A_2$ when $\vec{x}$, $\vec{x}^2$, and $\vec{y}$ are given.

Once the system modeling matrices are estimated, Eq. (1) then comes into play when an embodiment is deployed in the field, but where now $A_1$ and $A_2$ are known, $\vec{y}$ is measured, and $\vec{x}$ is to be estimated. Various well known numerical techniques may be applied to eq. (1) to estimate $\vec{x}$ for a given $A_1$, $A_2$, and $\vec{y}$, and one or more criteria of goodness are chosen for modules 414 and 418 to determine whether a target analyte or functional group is present.

Figure 5:
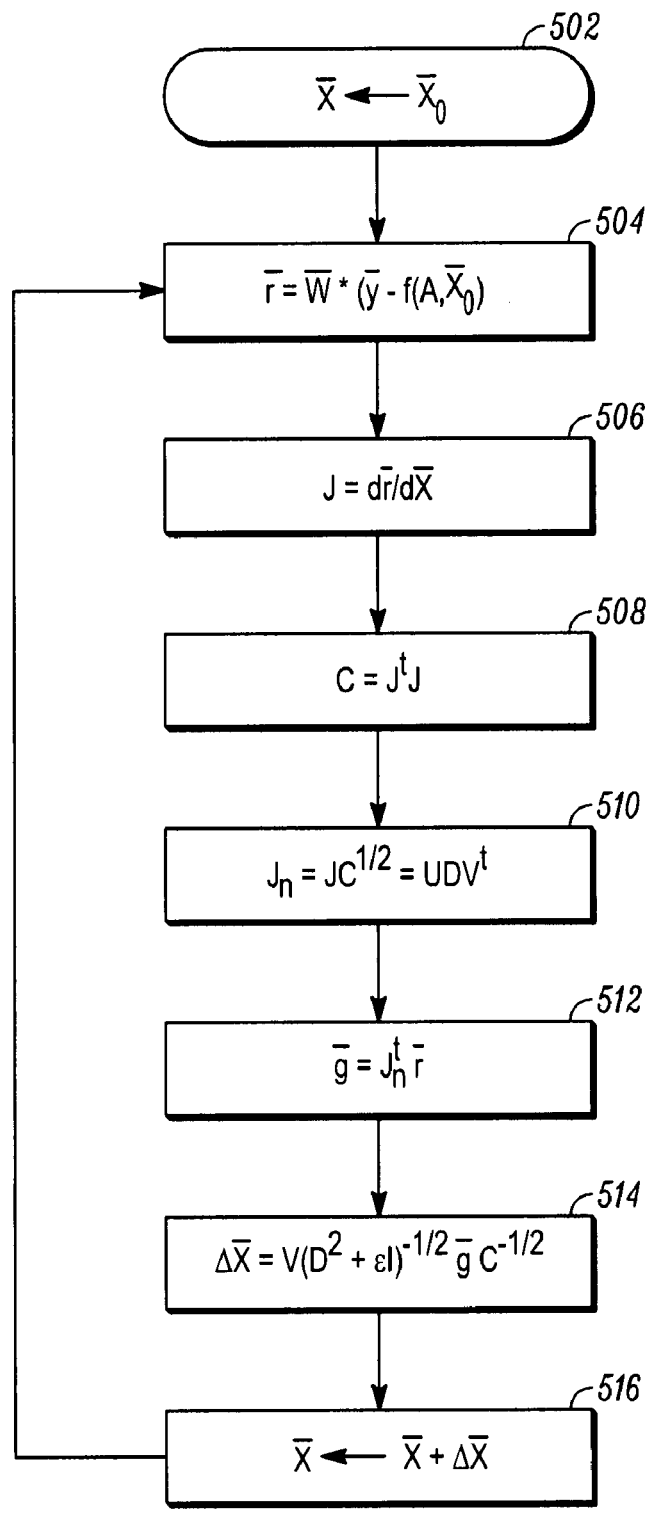
FIG. 5 illustrates a flow diagram for estimating gas or liquid concentrations gas according to an embodiment.

It has been found for some embodiments that a numerical technique based upon a modification to the Levenberg Marquart Nonlinear Least Squares method, outlined in the flow diagram of FIG. 5, may be of utility in estimating the concentrations from Eq. (1) for a given $A_1$, $A_2$, and $\vec{y}$.

Referring to FIG. 5, the loop comprising modules 504 through 516 updates a concentration vector $\vec{x}$ according to (module 516)

$$\vec{x} \leftarrow \vec{x} + \Delta \vec{x},$$

where $\Delta \vec{x}$ is a correction vector.

A correction vector is generated as follows. Some initial starting point for the concentration vector $\vec{x}$, denoted as $\vec{x}_0$, is chosen in module 502. In module 504, each component in the residual vector $\vec{y} - f(A, \vec{x})$ is weighted according to a weight vector $\vec{w}$ to provided a weighted residual vector $\vec{r}$, where $$\vec{r} = \vec{w} * (\vec{y} - f(A, \vec{x})),$$

where * denotes component by component multiplication. The Jacobian matrix J is calculated in module 506, $$J = d\vec{r}/d\vec{x},$$

and the curvature matrix C is calculated in module 508, $$C = J^\dagger J,$$

where † denotes transposition and complex conjugation (the Hermitian adjoint operation). In module 510, the matrix $J_n$ is calculated based upon the Jacobian and curvature matrices, $$J_n = JC^{1/2},$$

followed by a singular value decomposition $$J_n = UDV^\dagger.$$

A gradient vector g is calculated in module 512 according to $$\vec{g} = J_n^\dagger \vec{r}.$$

In module 514, for some suitably chosen epsilon E, a correction vector $\Delta \vec{x}$ is calculated $$\Delta \vec{x} = V(D^2 + \epsilon I)^{-1/2} \vec{g} C^{-1/2},$$

where I is an identity matrix chosen so that the dimension of $\epsilon I$ matches that of D.

The loop comprising modules 504 through 516 may be repeated for various values of $\epsilon$. For some embodiments, a series of candidate values for $\epsilon$ such as $\epsilon = \{10^{-2}, 10^{-1}, 1, 10^2, 10^4\}$ may be chosen. On the first iteration of the loop comprising modules 504 through 516, a search may be made through the series for $\epsilon$ to find an $\vec{x}$ that results in the smallest norm (smallest sum of squares of the components) of the residual vector. For subsequent iterations, the previously used values in the series for $\epsilon$ may be multiplied by the previous found value for $\epsilon$ that produced the minimum norm of the residual vector $\vec{r}$. With the updated series, a search is again made for the best $\epsilon$ as was done in the previous iteration. This process may be stopped after some chosen criterion of goodness is satisfied. Criteria of goodness other than the norm of the residual vector may be considered in finding the best $\epsilon$. For example, a minimum norm criterion in conjunction with a criterion based on the least number of significant components in the $\vec{x}$ vector may be combined into a criterion of goodness.

The above-described method for updating the concentration vector over several iterations of the loop comprising modules 504 through 516 may then be performed for various starting points $\vec{x}_0$. For some embodiments, the various starting points may be chosen randomly (or more practically, pseudorandomly.) Some criterion of goodness, such as the norm of the residual vector, may be considered when choosing the final result for the various starting points.

Figure 6:
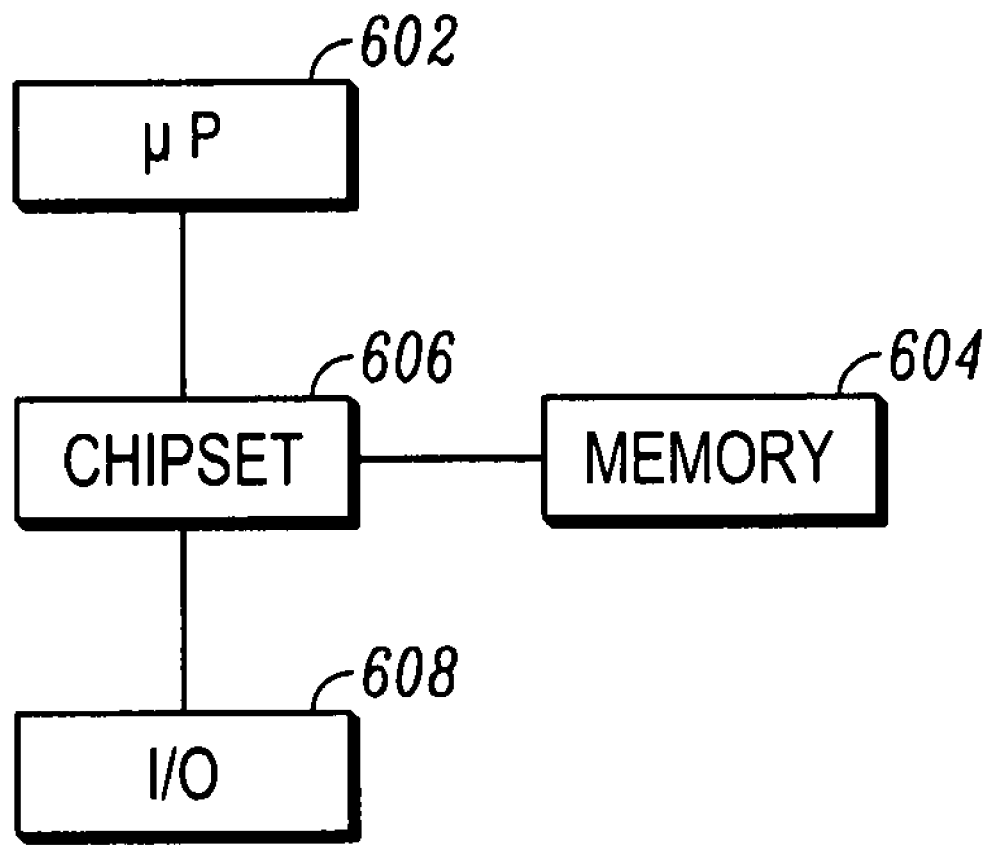
FIG. 6 illustrates a prior art computer system for implementing various modules in the flow diagrams of FIGS. 4 and 5.

As discussed with respect to the flow diagram of FIG. 4, the various modules in FIG. 5 may be implemented in special purpose hardware, by software running on a programmable machine, firmware, or some combination thereof. FIG. 6 illustrates, at a high level, a portion of a computer system, for implementing some of the modules illustrated in FIGS. 4 and 5. For the computer system of FIG. 6, microprocessor 602 communicates with memory 604 by way of chipset 606. Chipset 606 may be realized in one or more die, or some or all of its functions may be integrated with microprocessor 602. Memory 604 may represent a hierarchy of memory. Chipset 606 also provides communication to I/O (Input/Output) module 608, which may be coupled to bus 108. Software for performing various modules in FIGS. 4 and 5 may reside in memory 604.

Various polymers may be chosen for the sensor films. Examples are: Poly (4-vinylphenol-co-methyl methacrylate); Poly (ethylene-co-acrylic acid); Poly (styrene-co-maleic acid); Poly (2-vinyl pyridine); Poly (4-vinylpyridine); Vinyl alcohol/vinyl butyral copolymer; Cyanoethyl hydroxyethyl cellulose; Soluble polyimide; Polyepichlorohydrin; Poly (epichlorohydrin-co-ethylene oxide); and Polyethylene oxide.

Although the subject matter has been described in language specific to structural features and methodological acts, it is to be understood that the subject matter defined in the appended claims is not necessarily limited to the specific features or acts described above. Rather, the specific features and acts described above are disclosed as example forms of implementing the claims. Accordingly, various modifications may be made to the described embodiments without departing from the scope of the invention as claimed below.

Throughout the description of the embodiments, various mathematical relationships are used to describe relationships among one or more quantities. For example, a mathematical relationship or mathematical transformation may express a relationship by which a quantity is derived from one or more other quantities by way of various mathematical operations, such as addition, subtraction, multiplication, division, etc. Or, a mathematical relationship may indicate that a quantity is larger, smaller, or equal to another quantity. These relationships and transformations are in practice not satisfied exactly, and should therefore be interpreted as "designed for" relationships and transformations. One of ordinary skill in the art may design various working embodiments to satisfy various mathematical relationships or transformations, but these relationships or transformations can only be met within the tolerances of the technology available to the practitioner.

Accordingly, in the following claims, it is to be understood that claimed mathematical relationships or transformations can in practice only be met within the tolerances or precision of the technology available to the practitioner, and that the scope of the claimed subject matter includes those embodiments that substantially satisfy the mathematical relationships or transformations so claimed.

What is claimed is:

1. A system comprising:
a set of sensors, each sensor having a resistance indicative of gas or liquid sorption by the sensor; and
a processing system to estimate values of a time derivative of resistance at various times for each sensor,
the processing system to estimate event occurrences for each sensor by comparing for each sensor the estimated values of the time derivative of the resistance to a threshold, and the processing system to estimate baseline resistance for each sensor, and to provide for each sensor for each event occurrence a response indicative of a change in the resistance divided by the baseline resistance associated with each event occurrence.

2. The system as set forth in claim 1, further comprising a sensor to measure humidity;
the processing system to subtract from each response associated with each event occurrence a humidity response associated with each event occurrence based upon the measured humidity.

3. A system comprising:
a set of sensors, each sensor having a resistance indicative of gas or liquid sorption by the sensor;
a processing system to estimate values of a time derivative of resistance at various times for each sensor; and
a sensor to measure humidity;
the processing system to subtract from a response associated with an event occurrence for each sensor a humidity response associated with each event occurrence based upon the measured humidity.

4. A system comprising,
a set of n sensors, each sensor having a resistance R(i) indicative of gas or liquid sorption, where $i \in [1, n]$ is an index indicating a sensor; and
a processing system to process a set of resistance measurements for each sensor for a set of times, the processing system to estimate time derivatives dR(i)/dt for the set of times and to declare an event occurrence if there is a sensor i for which the estimate of the time derivative dR(i)/dt satisfies a relationship with a threshold; and
the processing system to provide a set of responses $dR(j)/R_0(j)$ for an event occurrence, where j is an index indicating a sensor belonging to the set of n sensors and $j \in S$ where S is a subset of $[1, n]$, $S \subset [1, n]$, where dR(j) is a difference in resistance values for sensor j associated with the event occurrence and $R_0(j)$ is an estimated baseline resistance value for sensor j associated with the event occurrence.

5. The system as set forth in claim 4, further comprising:
a humidity sensor to provide a measure of humidity; and
the processing system to provide a humidity response $dR_H(j)/R_{0H}(j)$ for $j \in S$ at the event occurrence based upon the measure of humidity, and to subtract the humidity response $dR_H(j)/R_{0H}(j)$ from the set of responses $dR(j)/R_0(j)$ to provide components for a vector response $\vec{y}$.

6. The system as set forth in claim 5, the processing system to provide a vector of concentrations $\vec{x}$ to satisfy a criterion of goodness based upon a residual vector $\vec{y}-f(A, \vec{x})$ where $f(A, \vec{x})$ is a function of the vector of concentrations $\vec{x}$ and system modeling parameter A.

7. The system as set forth in claim 6, where the function $f(A, \vec{x})$ is given by $f(A, \vec{x}) = A_1 \vec{x} + A_2 \vec{x}^2$, where the $i^{th}$ component of $\vec{x}^2$ is the square of the $i^{th}$ component of $\vec{x}$, where $A_1$ and $A_2$ are matrices representing system modeling parameter A.

8. The system as set forth in claim 6, where the criterion of goodness is based upon a weighted residual $$\vec{r} = \vec{w} * (\vec{y} - f(A, \vec{x})),$$

where * denotes component by component multiplication.

9. The system as set forth in claim 8, where the vector of concentrations $\vec{x}$ is updated by an update vector $\Delta \vec{x}$ where $$\Delta \vec{x} = V(D^2 + \epsilon I)^{-1/2} \vec{g} C^{-1/2},$$

where $\in$ is a scalar, where a Jacobian matrix J is calculated, $$J = d\vec{r}/d\vec{x},$$

and a curvature matrix C is calculated, $$C = J^\dagger J,$$

where †denotes transposition and complex conjugation, where a matrix $J_n$ is calculated based upon the Jacobian and curvature matrices, $$J_n = JC^{1/2},$$

followed by a singular value decomposition $$J_n = UDV^\dagger$$

where $\vec{g}$ is calculated according to $$\vec{g} = J_n^\dagger \vec{r}.$$

where I is an identity matrix chosen so that the dimension of $\in$I matches that of D.

* * * * *